(12) United States Patent
Jensen et al.

(10) Patent No.: US 8,414,881 B2
(45) Date of Patent: *Apr. 9, 2013

(54) METHOD FOR ENHANCING STEM CELL TRAFFICKING

(75) Inventors: Gitte S. Jensen, Port Dover (CA); Christian Drapeau, Keno, OR (US)

(73) Assignee: Desert Lake Technologies, LLC, Keno, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/227,323

(22) Filed: Sep. 7, 2011

(65) Prior Publication Data

US 2011/0318310 A1 Dec. 29, 2011

Related U.S. Application Data

(63) Continuation of application No. 12/033,801, filed on Feb. 19, 2008, now Pat. No. 8,034,328, which is a continuation of application No. 10/946,561, filed on Sep. 20, 2004, now abandoned, which is a continuation of application No. 10/145,081, filed on May 13, 2002, now Pat. No. 6,814, 961.

(60) Provisional application No. 60/290,920, filed on May 14, 2001.

(51) Int. Cl.
*A01N 63/00* (2006.01)
*A01N 63/02* (2006.01)
*C12N 1/12* (2006.01)

(52) U.S. Cl. ............... 424/93.1; 424/195.17; 435/257.1; 435/946

(58) Field of Classification Search .................. None
See application file for complete search history.

(56) References Cited

U.S. PATENT DOCUMENTS

| | | | |
|---|---|---|---|
| 5,585,365 A | 12/1996 | Hayashi et al. | |
| 6,261,549 B1 | 7/2001 | Fernandez et al. | |
| 6,511,800 B1 | 1/2003 | Singh | |
| 6,814,961 B1 | 11/2004 | Jensen et al. | |
| 7,205,284 B2 | 4/2007 | Pasco et al. | |
| 2010/0092507 A1 | 4/2010 | Jensen et al. | |
| 2010/0209461 A1 | 8/2010 | Jensen et al. | |

FOREIGN PATENT DOCUMENTS

| | | |
|---|---|---|
| JP | 56063911 A | 5/1981 |
| JP | 2000253853 | 9/2000 |
| WO | WO 02/04000 | 1/2002 |
| WO | WO 2004/066969 | 8/2004 |

OTHER PUBLICATIONS

Ramamoorthy et al. "Effect of supplementation of Spirulina on hypercholesterolic patients". Journal of Food Science and Technology. 1996, vol. 33, No. 2, pp. 124-127 (STN Biosis abstract 1996:466807/accession number).*

"Adult Stem Cells Enhancement, New Breakthrough Product: StemEnhance™ from StemTech Health Sciences, Inc.," http://www.astrologyzine.com/stemtech-stemenhance-stem-cell-enhancer.shtml (9 pages), downloaded Jun. 13, 2006.

"StemEnhance™ The first Stem Cell Enhancer" published by StemTech HealthSciences, Inc., http://www.stemtechhealth.com (1 page), downloaded Jun. 13, 2006.

Azizi S.A., et al., "Engraftment and migration of human bone marrow stromal cells implanted in the brains of albino rats-similarities to astrocyte grafts," *Proc Natl Acad Sci USA*, 95(7):3908-13, (1998).

Barrett, "StemTech's Dubious Claims," http://www.mlmwatch.org/04C/Stemtech/stemtech.html (4 pages), downloaded Jun. 13, 2006.

Benedetti et al., "Antioxidant properties of a novel phycocyanin extract from the blue-green alga," *Aphanizomenon flos-aquae, Life Sciences*, 75:2353-5362, 2004.

Bhat and Madyastha, "C-Phycocyanin: A Potent Peroxyl Radical Scavenger in Vivo and in Vitro," *Biochemical and Biophysical Research Communications*, 275:20-25, 2000.

Bouillenne-Walraud et al. Arch. Inst. Bot., Liege, 14(5):23. Abstract from STN CAPLUS accession No. 1939:54290 (1937).

Brazelton, T.R., et al., "From marrow to brain: expression of neuronal phenotypes in adult mice," *Science*, 290(5497):1775-9, (2000).

Cousens, G., "Report of Treatment of Alzheimer's Disease with Alphanae Klamathomenon Flos-Aqua," *Orthomedicine*, 8:(1 & 2), 2000.

Eglitis, J., et al., "Hematopoietic cells differentiate into both microglia and macroglia in the brains of adult mice," *Proc Natl Acad Sci USA*, 94(8):4080-5, (1997).

Environmental Health Perspectives. 107(1), printout pp. 1-5 from website http://www.ehponline.org/docs/1999/107-1/forum.html (1999).

Fallon, J., et al., "In vivo induction of massive proliferation, directed migration, and differentiation of neural cells in the adult mammalian brain," *Proc Natl Acad Sci USA*, 97(26):14686-91, (2000).

Ferrari, G., et al., "Muscle regeneration by bone marrow-derived myogenic progenitors," *Science*, 279(5356):1528-30, (1998).

Frenette, P.S., and Weiss, L., "Sulfated glycans induce rapid hematopoietic progenitor cell mobilization: evidence for selectin-dependent and independent mechanisms," *Blood*, 96(7):2460-2468, (2000).

González et al., "Anti-Inflammatory Activity of Phycocyanin Extract in Acetic Acid-Induced Colitis in Rats," *Pharmacological Research*, 39(1):55-59, 1999.

Hickey, W.F., "Leukocyte traffic in the central nervous system: the participants and their roles," *Semin Immunol*, 11(2):125-37, (1999).

Hidalgo, A., et al., *Exp. Hematol.*, 29(3):345-55, (2001).

Jensen et al., "Consumption of *Aphanizomenon flos-aquae* Has Rapid Effects on the Circulation and Function of Immune Cells in Humans," *JANA*, 2(3):50-58, 2000.

Knopf P.M., et al, "Antigen-Dependent Intrathecal Antibody Synthesis in Normal Rat Brain: Tissue Entry and Local Retention of Antigen-Specific B Cells." *J. Immunol.*, 161, p. 692, (1998).

(Continued)

*Primary Examiner* — Vera Afremova
(74) *Attorney, Agent, or Firm* — Klarquist Sparkman, LLP

(57) ABSTRACT

Consumption of blue-green algae, or extracts thereof, enhances trafficking or homing of stem cells in animals by inducing a transient increase in the population of stem cells present in the animal's circulatory system. The animal may be healthy or suffering some disease or physiological condition.

17 Claims, 7 Drawing Sheets

OTHER PUBLICATIONS

Koc, O.N. and Lazarus, H.M., "Mesenchymal stem cells: heading into the clinic," *Bone Marrow Transplant*, 27(3):235-9, (2001).

Kocher, A.A., et al., "Neovascularization of ischemic myocardium by human bone-marrow-derived angioblasts prevents cardiomyocyte apoptosis, reduces remodeling and improves cardiac function," *Nat Med*, 7:430-36, (2001).

Kollet, O., et al., *Blood*, 97(10):3283-91, (2001).

Kopen, G.C., et al., "Marrow stromal cells migrate throughout forebrain and cerebellum, and they differentiate into astrocytes after injection into neonatal mouse brains," *Proc Natl Acad Sci USA*, 96(19):10711-6, (1999).

Kumar et al., "Bioregulatory and therapeutic effects of blue green algae," *Indian J. Microbiology* 43(1):9-16, (Mar. 2003).

Kushak et al., Book of Abstracts, 217th ACS National Meeting, Calif., March 21025, AGFD-045 (1999).

Kushak, et al., "Favorable Effects of Blue-Green Algae *Aphanizomenon flos-aquae* on Rat Plasma Lipids," *JANA*, 2(3):59-65, 2000.

Kushak, et al., "The Effect of Blue-Green Algae *Aphanizomenon Flos-Aquae* on Nutrient Assimilation in Rats," *JANA*, 3(4):35-39, 2001.

Lagasse, E., et al., "Purified hematopoietic stem cells can differentiate into hepatocytes in vivo," *Nat Med*, 6(11):1299-35, (2000).

Lahitová et al., "Antimutagenic Properties of Fresh-Water Blue-Green Algae," *Folia Microbiol.*, 39(4):301-303, 1994.

Lasley, E.N., "Death Leads to Brain Neuron Birth," *Science*, 288(5474):2111-12, (2000).

Magavi S.S., et al., "Induction of neurogenesis in the neocortex of adult mice," *Nature*, 405(6789):892-3, 895, (2000).

Mattson, M.P., "Emerging neuroprotective strategies for Alzheimer's disease: dietary restriction, telomerase activation, and stem cell therapy," *Exp Gerontol*, 35(4):489-502, (2000).

Mattson, M.P., "Existing data suggest that Alzheimer's disease is preventable," *Ann N Y Acad Sci*, 924:153-9, (2000).

Mezey, E., et al., "Turning blood into brain: cells bearing neuronal antigens generated in vivo from bone marrow," *Science*, 290(5497):1779:82, (2000).

Orlic D., et al., "Bone marrow cells regenerate infarcted mycardium," *Nature*, 410(6829):701-5, (2001).

Ostensvik et al., "Antibacterial properties of extracts from selected planktonic freshwater *Cyanobacteria*—a comparative study of bacterial bioassays," *Journal of Applied Microbiology*, 84:1117-1124, 1998.

Pereira, R.F., et al., "Marrow stromal cells as a source of progenitor cells for nonhematopoietic tissues in transgenic mice with a phenotype of osteogenesis imperfecta," *Proc Natl Acad Sci USA*, 95(3):1142-7, (1998).

Petersen, B.E., et al., "Bone marrow as a potential source of hepatic oval cells," *Science*, 284(5417):1168-70, (1999).

Polli, E.E., "Transplanting bone-marrow stem cells in the central nervous system," *Haematologica*, 85(10):1009-10, (2000).

Prockop, D.J., et al, "Potential use of stem cells from bone marrow to repair the extracellular matrix and the central nervous system," *Biochem Soc Trans*, 28(4):341-5, (2000).

Pugh and Pasco, "Characterization of human monocyte activation by a water soluble preparation of *Aphanizomenon flos-aquae*," *Phytomedicine*, 8(6):445-453, 2001.

Pugh, et al., *Planta Med*, 67:737-42, (2001).

Reddy et al., "Selective Inhibition of Cyclooxygenase-2 by C-Phycocyanin, a Biliprotein from *Spirulina platensis*," *Biochemical and Biophysical Research Communications*, 277:599-603, 2000.

Remirez et al., "Effect of Phycocyanin in Zymosan-Induced Arthritis in Mice—Phycocyanin as an Antiarthritic Compound," *Drug Development Research*, 48:70-75, 1999.

Rimbau et al., "C-Phycocyanin protects cerebellar granule cells from low potassium/serum deprivation-induced apoptosis," *Naunyn-Schmiedeberg's Arc Pharmacol*, 364:96-104, 2001.

Rimbau et al., "Protective effects of C-phycocyanin against kainic acid-induced neuronal damage in rat hippocampus," *Neuroscience Letters*, 276:75-78, 1999.

Romay and González, "Phycocyanin is an Antioxidant Protector of Human Erythrocytes Against Lysis by Peroxyl Radicals," *J. Pharm. Pharmocol.*, 52:367-368, 2000.

Romay et al., "Antioxidant and anti-inflammatory properties of C-phycocyanin from blue-green algae," *Inflamm. Res.*, 47:36-41, 1998.

Romay et al., "Effects of Phycocyanin Extract on Prostaglandin $E_2$ Levels in Mouse Ear Inflammation Test," *Arzneim.-Forsch./Drug Res.* 50(II), 1106-1109, 2000.

Romay et al., "Further studies on anti-inflammatory activity of phycocyanin in some animal models of inflammation," *Inflamm. Res.*, 57:334-338, 1998.

Romay et al., "Phycocyanin Extract Reduces Leukotriene $B_4$ Levels in Arachidonic Acid-induced Mouse-ear Inflammation Test," *J. Pharm. Pharmocol.*, 51:641-642, 1999.

Schaeffer and Krylov, "Anti-HIV Activity of Extracts and Compounds from Algae and *Cyanobacteria*," *Ecotoxicology and Environmental Safety*, 45:208-227, 2000.

Sweeney, E.A., et al., "Mobilization of stem/progenitor cells by sulfated polysaccharides does not require selectin presence," *PNAS*, 97(12):6544-6549, (2000).

Vadiraja et al., "Hepatoprotective Effect of C-Phycocyanin: Protection for Carbon Tetrachloride and R-(+)-Pulegone-Mediated Hepatotooxicty in Rats," *Biochemical and Biophysical Research Communications*, 249:428-431, 1998.

Williams, K.C. and Hickey, W.F., "Traffic hematogenous cells through the central nervous system," *Curr Top Microbiol Immunol*, 202:221-45, (1995).

Zhang Cheng-Wu, et al., "Effects of polysaccharaide and phycocyanin from spirulina on peripheral blood and hematopoietic system of bone marrow in mice," Nanjing Univ. China, Proc. of Second Asia Pacific Conf. on Algal Biotech., Univ. of Malaysia, China (Apr. 1994).

* cited by examiner

METHOD FOR ENHANCING STEM CELL TRAFFICKING

PRIORITY CLAIM

This application is a continuation of U.S. patent application Ser. No. 12/033,801, filed Feb. 19, 2008, which issued as U.S. Pat. No. 8,034,328 on Oct. 11, 2011, which is a continuation of U.S. patent application Ser. No. 10/946,561, filed Sep. 20, 2004, now abandoned, which is a continuation of U.S. patent application Ser. No. 10/145,081, filed May 13, 2002, which issued as U.S. Pat. No. 6,814,961 on Nov. 9, 2004, which claims the benefit of U.S. Provisional Patent Application No. 60/290,920, filed on May 14, 2001, which are all incorporated by reference herein in their entirety.

FIELD

This invention relates to methods of enhancing animal stem cell trafficking, specifically to the use of blue green algae, or a biological component thereof, to enhance the trafficking or homing of such stem cells.

BACKGROUND

Stem cells are pluripotent cells derived from somatic tissue capable of differentiating into more specialized cells. For example, hematopoietic stem cells can differentiate into many different types of blood cells, including red blood cells, platelets, and leukocytes.

Hematopoietic stem cells are quite abundant and play a role in the continuous lifelong physiological replenishment of blood cells. Stem cells develop into both hematopoietic lineage cells and non-hematopoietic, tissue specific cells. Recently, stem cells have been found to differentiate into a variety of tissue-specific cell types, such as myocytes, hepatocytes, osteocytes, glial cells, and neurons. For example, stem cells have been shown to cross the blood-brain barrier (Williams and Hickey, *Curr. Top. Microbiol. Immunol.* 202: 221-245, 1995) and differentiate into neurons (Mezey, *Science* 290:1779-82, 2000). Thus, it is possible that stem cells could be used to treat Parkinson's disease (Polli, *Haematologica* 85:1009-10, 2000), Alzheimer's disease (Mattson, *Exp. Gerontol.* 35:489-502, 2000), and traumatic brain injury (Magavi, *Nature* 405: 892-3, 895, 2000). Stem cells also have been shown to differentiate into fibroblast or fibroblast-like cells, and to express collagen (Periera et al., *Proc. Natl. Acad. Sci.* 95:1142-7, 1998). Thus, it is possible that stem cells can be used to treat osteogenesis imperfecta and bone fractures. Peterson et al. (*Science* 284:1168-70, 1999) also have shown that liver cells can arise from stem cells. Thus, stem cells may be of use in treating a variety of pathologies of the liver, including, but not limited to cirrhosis. In addition, bone marrow derived stem cells have been demonstrated to migrate to the site of a myocardial infarction and form myocardium (Orlic, *Nature* 410:701-5, 2000). Thus, stem cells may be use in treating myocardial infarction.

Since stem cells are capable of differentiating into a broad variety of cell types, they play an important role in the healing and regenerative processes of various tissues and organs. See Koc, O. N., and Lazarus, H. M., *Bone Marrow Transplant*, 27(3):235-39 (2001). Bone marrow stem cells, including marrow stromal cells (MSCs), injected into a recipient's circulatory system can integrate into various organs and tissues to become mature, terminally differentiated cells. Therefore, activation and enhancement of stem cell trafficking can amplify these physiological processes and provide a potential therapy for various pathologies.

SUMMARY

A method is disclosed herein for enhancing trafficking of stem cells by administering a therapeutically effective amount of blue green algae to a subject. In one embodiment, whole cells of a blue-green algae, or extracts thereof, are administered to the subject to enhance stem cell trafficking. The algae cells may be fresh, dehydrated, or preserved in some manner. In another embodiment, a high-molecular weight polysaccharide fraction of the blue green algae is administered to the subject. Pharmaceutical compositions including a therapeutically effective amount of a blue green algae, or a component thereof, are disclosed herein.

In one embodiment, a therapeutically effective amount of blue-green algae induces a transient increase in the population of some stem cells, such as CD34+ stem cells, in the subject's circulatory system. The percentage increase in the number of circulating stem cells, compared to a control, is more than about 10%, more than about 25%, more than about 50%, more than about 100%, more than about 200%, more than about 400%, or more than about 500% following administration of the blue green algae. Additionally, administration of certain fractions of whole AFA can increase the homing of stem cells to various parts of the body, evidenced by a decrease in the number of circulating stem cells. For example, administration of a polysaccharide rich fraction of whole AFA increases the homing of CD34+ and NK cells from the circulatory system to various parts of the body.

In some embodiments, the subject provided the blue-green algae is healthy. In other embodiments, the subject suffers a disease or physiological condition.

BRIEF DESCRIPTION OF THE DRAWINGS

FIG. 4A is a flow cytometry profile of blood taken from the volunteer subject prior to consumption of AFA and FIG. 4B is a flow cytometry profile of blood taken from the same subject 2 hours after consumption of 5 grams whole AFA.

DETAILED DESCRIPTION

Figure 1:
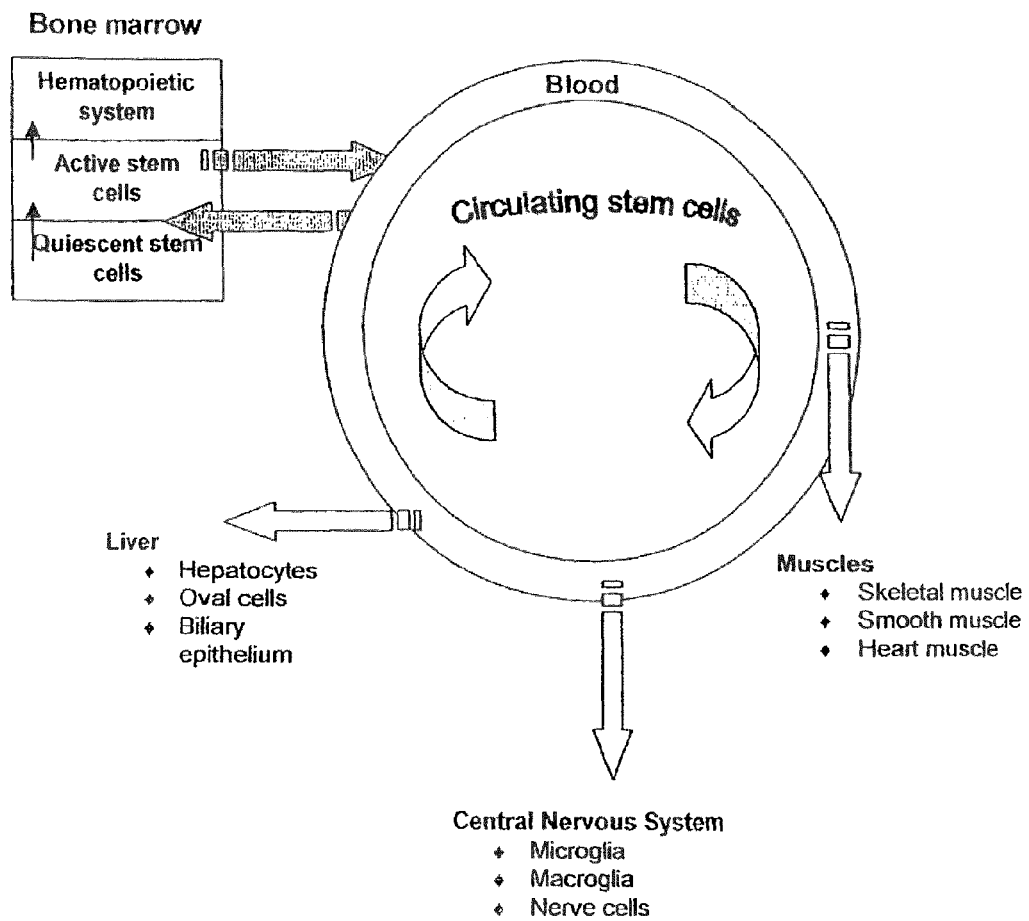
FIG. 1 is a schematic illustration of the pathway of stem cells entering the circulatory system and various organs and systems.

Consumption of blue-green algae, such as, but not limited to, *Aphanizomenon flos aquae* (AFA), induces mobilization of endogenous stem cells into the circulatory system where they may come into contact with multiple organs and tissues. Since these stem cells are capable of migrating into various tissues and organs and differentiating into functional cells, consumption of blue-green algae proves tissue regeneration and anti-aging therapies.

The following explanations of terms are provided to better illustrate the present invention. Explanations of common terms also can be found in Rieger et al., *Glossary of Genetics: Classical and Molecular*, 5th edition, Springer-Verlag: New York, 1991; Lewin, Genes VII, Oxford University Press: New York, 1999; *Dictionary of Bioscience*, Mcgraw-Hill: New York 1997; Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Explanations of Terms

Administration to a subject. Providing blue-green algae to a subject includes administering whole blue-green algae cells or extracts of blue-green algae cells. Routes of administration include, but are not limited to, oral and parenteral routes, such as intravenous (IV), intraperitoneal (IP), rectal, topical, ophthalmic, nasal, and transdermal. Oral administration includes both whole blue-green algae and orally bioavailable extracts of blue-green algae. If administered orally, the whole cells or extracts may be provided or administered in the form of a unit dose in solid, semi-solid, or liquid dosage form such as tablets, pills, powders, liquid solutions, or liquid suspensions. However, extracts of blue-green algae also may be administered intravenously in any conventional medium for intravenous injection, such as an aqueous saline medium, or in a blood plasma medium. The medium also may contain conventional pharmaceutical adjunct materials, such as pharmaceutically acceptable salts to adjust the osmotic pressure, lipid carriers (e.g., cyclodextrins), proteins (e.g., serum albumin), hydrophilic agents (e.g., methyl cellulose), detergents, buffers, preservatives, and the like. A more complete explanation of acceptable pharmaceutical carriers can be found in *Remington: The Science and Practice of Pharmacy* ($19^{th}$ Edition, 1995) in chapter 95.

Agent that affects hematopoiesis. A compound, antibody, nucleic acid molecule, protein, or cell that affects hematopoiesis. A molecular agent can be a naturally occurring molecule or a synthetic molecule. In some embodiments, the agent affects the growth, proliferation, maturation, or differentiation or release of hematopoietic cells. In one embodiment, the agent is a blue green algae, or an extract or component of a blue green algae cell.

Agent that affects stem cell circulation. A compound, antibody, nucleic acid molecule, protein, or cell, including neuropeptides and other signaling molecules, that affects the release of stem cells into the circulatory system, as well as homing from the circulatory system into tissue. A molecular agent may be a naturally occurring molecule or a synthetic molecule. In one specific, non-limiting example, the agent is a blue-green algae. In another specific, non-limiting example, the agent is a extract of blue green algae, or an isolated component or compound extracted from blue-green algae, such as a compound found in a polysaccharide-rich fraction (fraction A) of blue-green algae extract.

An agent that affects stem cell circulation may affect the ratio of stem cells in the quiescent pool versus the active pool. In some embodiments, the agent affects the balance between undifferentiated stem cells and stem cells differentiating into $CD34^{Low}$ and $CD34^{high}$ cells. In other embodiments, the agent affects the release or differentiation of stem cells, such as $CD34^{high}$ (CD34+) cells.

Animal. A living, multicellular, vertebrate organism including, for example, mammals, fish, reptiles, and birds.

Blue-green algae. Common name for gram-negative photosynthetic bacteria belonging to Division Cyanophyta that may exist in unicellular, colonial, or filamentous forms. Representative blue-green algae include, but are not limited to, *Spirulina* species and *Aphanizomenon* species. *Aphanizomenon flos aquae* (AFA) is one specific, non-limiting type of blue-green algae.

The term "algae" is the plural form of "alga," which is a cell of a microalgae species. For example (and without limitation), "blue green algae" refers to multiple cells of a single *Aphanizomenon* species, multiple cells of a single *Spirulina* species, or a mixture of cells from multiple *Aphanizomenon* and/or *Spirulina* species.

Circulatory system. In animals, the circulatory system is composed of the structures that move blood and blood components throughout the body, including the vascular and lymph systems. The components of the circulatory system include the heart, blood vessels (arteries, veins, and capillaries), and lymph vessels.

Circulating stem cell. A stem cell present in the circulatory system.

Component of blue green algae. Any fraction, extract, or isolated or purified molecule from a blue green algae cell. In one embodiment, the component is a protein or nucleic acid. In another embodiment, the component is a component is a phytochemical. In another embodiment, the component is a fraction of a blue green algae. Thus, the blue green algae is disrupted, an inorganic or organic solvent is added, and fractions are collected. Specific, non-limiting examples are fractions are isolated using high performance liquid chromatography, thin layer chromatography, or distillation. In one embodiment, fractionation is based on the molecular weight or the hydrophobicity of the components of the blue green algae.

Differentiation. The process by which cells become more specialized to perform biological functions. Differentiation is a property that is often totally or partially lost by cells that have undergone malignant transformation.

Effective amount. An amount of blue-green algae or extract thereof capable of activating or enhancing stem cell trafficking (stem cell mobilization, stem cell homing), that can be determined by various methods used in the biological sciences, including generating an empirical dose-response curve. In one embodiment, a "therapeutically effective amount" is an amount effective for enhancing mobilization of stem cells that replenish, repair, or rejuvenate tissue. In another embodiment, a "therapeutically effective amount" is an amount effective for enhancing trafficking of stem cells. In still another embodiment, the "therapeutically effective amount" is an amount effective for enhancing homing of stem cells from the circulatory system to various tissues or organs.

A therapeutically effective amount also may be an amount sufficient for treating a condition or disease, such as an amount sufficient to relieve symptoms associated with nervous system disorders (for example, Alzheimer's disease, Parkinson's disease, multiple sclerosis, attention deficit disorder), traumatic brain or spinal cord injury), hypertension, liver disease, chronic fatigue syndrome, irritable bowel syndrome, bacterial or viral infections, mood disorders (for example, depression) or disorders of bone or cartilage.

In one specific, non-limiting example, the effective amount of blue-green algae is from about 0.01 to about 1.0 g per kg body weight, such as about 0.05 to about 0.5 g per kg body weight, or from about 0.1 to about 0.5 g per kg body weight. In another specific, non-limiting, example the effective amount of blue-green algae is from about 0.5 g to about 15 g, of from about 1 g to about 10 g, or from about 1 g to about 5 g. In one specific, non-limiting example, the effective amount of blue-green algae is 5 g. This effective amount may be administered at a given frequency, such as about once a week, about twice a week, about three times a week, once a day, about twice a day, about three times a day, or more.

The effective amount of blue-green algae and frequency of administration may depend on a variety of factors, such as the genus or species of algae utilized, whether whole cells or an extract is administered to the subject, the general health of the subject being treated, and the physiological characteristics (e.g., height, weight, body fat percentage, metabolism, etc.) of the subject being treated.

Specific assays for determining an effective amount of blue-green algae are provided herein. In one specific, non-limiting example, different amounts of whole blue-green algae, such as AFA, are consumed by human subjects and the presence and/or quantity of stem cells (which can include subtypes of such cells) present in the circulatory system is detected and/or analyzed. In another embodiment, a animal (e.g. murine) model is utilized, and the population of newly integrated stem cells is monitored in various tissues (see the Examples below). The methods disclosed in the present invention have equal application in medical and veterinary settings. Therefore, the general term "subject being treated" is includes all vertebrates (for example, but not limited to, humans, apes, dogs, cats, mice, rats, rabbits, sheep, pigs, and cows).

Enhancement (enhancing). An increase in a particular parameter of a cell or organism. In one embodiment, enhancement refers to a 25%, 50%, 100% or greater than 100% increase in a parameter. In one specific, non-limiting example, enhancement of stem cell circulation refers to an increase in a population of the cells of a non-hematopoietic lineage, such as a 25%, 50%, 100%, 200%, 400%, 500%, or greater increase in the population of cells or the response of the population of cells. In one embodiment, the parameter is the mobilization of stem cells. In another embodiment, the parameter is the differentiation of stem cells. In yet another embodiment, the parameter is the homing of stem cells.

Erythrocytes. Red blood cells that carry oxygen to tissues of the body.

Hematopoiesis. The formation and development of blood cells. Hematopoiesis involves the proliferation and terminal differentiation of hematopoietic stem cells. In adult mammals, hematopoeisis is known to occur in bone marrow. Hematopoiesis is the production of hematopoietic cells including B Cells, T cells, cells of the monocyte macrophage lineage, and red blood cells.

Homing. The process of a cell migrating from the circulatory system into a tissue or organ. In some instances, homing is accomplished via tissue-specific adhesion molecules and adhesion processes.

Immunologically normal. "Immunologically normal" denotes a subject that displays immune system characteristics typical for the species to which the individual belongs. These typical characteristics include, among others, functioning B-cells and T-cells as well as structural cell components, called cell surface antigens, which act as the immunologic signature for a particular organism.

The use of such immunologically normal recipients means that an immunologically normal recipient's immune system, via its B-(humoral response) and T-(cellular response) cells, will identify the cell surface antigens of a foreign cell or an engrafted tissue as foreign. This recognition leads ultimately to an immune response against the cell or tissue, resulting in destruction of the cell or rejection of the graft. An immune response against an allogeneic tissue is known as host-versus-graft rejection.

Immunologically compromised. An "immunologically compromised" subject has a genotypic or a phenotypic immunodeficiency. A genotypically-immunodeficient subject has a genetic defect that results in an inability to generate either humoral or cell-mediated responses. A specific, non-limiting example of a genotypically immunodeficient subject is a genotypically immunodeficient mouse, such as a SCID mouse or a bg/nu/xid mouse (Andriole et al., *J. Immunol.* 135:2911 (1985); McCune et al., *Science* 241:1632 (1988)). A "phenotypically-immunodeficient subject" is a subject, which is genetically capable of generating an immune response, yet has been phenotypically altered such that no response is seen. In one specific, non-limiting example, a phenotypically-immunodeficient recipient is irradiated. In another specific, non-limiting example, a phenotypically-immunodeficient subject has been treated with chemotherapy. In yet another specific, non-limiting example, the phenotypically-immunodeficient subject has suffered a bacterial or viral infection, such as the human immunodeficiency virus (HIV) or simian immunodeficiency virus (SIV).

Inhibition (inhibiting). A decrease in a particular parameter of a cell or organism. In one embodiment, inhibition refers to a 25%, 50%, or 100% decrease in a parameter.

Isolated. An "isolated" biological component (such as a nucleic acid molecule, polypeptide, other biological molecule) has been substantially separated or purified away from other biological components of cells in which the component naturally occurs. An "isolated" cell has been substantially separated or purified away from other cells of different species (in the case of microorganisms) or cells of the organism (in the case of multicellular organisms). Nucleic acids and proteins may be isolated by standard purification methods, recombinant expression in a host cell, or chemically synthesized. Cells may be isolated by standard culturing methods. In one embodiment, the blue green algae is harvested from a natural source (e.g. Klamath Lake), and prepared by drying (see Example 1).

Leucocytes. White blood cells. Spherical, colorless, and nucleated corpuscles involved in with host defense, including immunological responses. Specific types of leucocytes include basophils, coelomocytes, eosinophils, haemocytes, lymphocytes, neutrophils, and monocytes.

Lymphocytes. A type of white blood cell that is involved in the immune defenses of the body. There are two main types of lymphocytes: B-cell and T-cells.

Lymphoproliferation. An increase in the production of lymphocytes.

Mammal. This term includes both human and non-human mammals. Similarly, the term "subject" includes both human and veterinary subjects.

Monocyte. A large white blood cell in the blood that ingests microbes or other cells and foreign particles. When a monocyte passes out of the bloodstream and enters tissues, it develops into a macrophage.

Muscle cell. A cell of striated, cardiac, or smooth muscle tissue. In striated (skeletal) muscle, a muscle cell is composed of a syncytium formed by the fusion of embryonic myoblasts. In smooth muscle, a muscle cell is a single cell characterized by large amounts of actin and myosin and capable of contracting to a small fraction of its overall length. In cardiac muscle, the muscle cell is linked to neighboring cells by specialized junctions called intercalated discs.

Pharmaceutically acceptable carriers. The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the blue-green algae and extracts described herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Platelets. Small cell fragments in blood derived from megacaryocytes. Platelets participate in blood clotting and pathological inflammatory processes.

Polysaccharide: A polymer of more than about ten monosaccharide residues linked glycosidically in branched or unbranched chains.

Progenitor cell. A cell that gives rise to progeny in a defined cell lineage. A "hematopoietic progenitor cell" is a cell that gives rise to cells of the hematopoietic lineage.

Recruitment of a stem cell. A process whereby a stem cell in the circulatory system migrates into a tissue or organ. Recruitment may be facilitated by a compound or molecule, such as a chemoattractant signal or cell receptor. For example, both CXCR4 and SDF-1 have identified roles in stem cell homing. Hidalgo, A., et. al., *Exp. Hematol.*, 29(3):345-55 (2001); Kollet, O., et al., *Blood*, 97(10)3283-91 (2001).

Satellite cell. A muscle-specific stem cell, often located in the periphery of muscle tissue, and capable of migrating into a muscle to aid in tissue repair and reconstruction.

Stem cell. A pluripotent cell that gives rise to progeny of many tissue types, including (but not limited to) the entire hematopoietic and marrow stromal cell lineages. A typical stem cell resides in the bone marrow, either as an adherent stromal cell type, or as a more differentiated cell that expresses CD34, either on the cell surface or in a manner where the cell is negative for cell surface CD34.

Subject. An animal that has a circulatory system, including vertebrates such as humans and other primates, canines, felines, bovines, and rodents.

Trafficking. The processes of movement of a cell from the tissue of origin and traveling within the circulatory system. In one embodiment, trafficking includes movement of a cell from the tissue of origin, homing by adhesion to the endothelium, transmigration, and final migration within the target organ. In one embodiment, tracking is the process of movement of a cell of the immune system. In another embodiment, trafficking includes stem cell mobilization. One specific, non-limiting example of trafficking is the movement of a stem cell to a target organ. Another specific, non-limiting example of trafficking is the movement of a B cell or a pre-B cell leaving the bone marrow and moving to a target organ.

Transplantation. The transfer of a cell population, tissue or an organ, or a portion thereof, from one body or part of the body to another body or part of the body. An "allogeneic transplantation" or a "heterologous transplantation" is transplantation from one individual to another, wherein the individuals have genes at one or more loci that are not identical in sequence in the two individuals. An allogeneic transplantation can occur between two individuals of the same species, who differ genetically, or between individuals of two different species. An "autologous transplantation" is a transplantation of a tissue or a portion thereof from one location to another in the same individual, or transplantation of a tissue or a portion thereof from one individual to another, wherein the two individuals are genetically identical.

Enhancing Stem Cell Mobilization, Differentiation, and Homing

A method is described herein for enhancing stem trafficking or mobilization by administering to a subject a therapeutically effective amount of a blue-green algae.

In one embodiment, a blue-green algae, such as *Aphanizomenon flos aquae* (AFA), is administered to a subject, though the subject may be provided a mixture of more than one blue-green algae. In some embodiments, the subject consumes and digests whole cells of a blue-green algae. The cells may be fresh, frozen, freeze-dried, dehydrated, or preserved in some other manner.

In alternative embodiments, an extract of the blue-green algae is provided or administered to the subject. Therefore, blue-green algae, as described herein, encompasses both whole algal cells and extracts thereof. The blue-green algae can be provided alone as an isolated or purified substance, or may be part of a composition including a pharmaceutically acceptable carrier. In one embodiment, a polysaccharide fraction is administered to the subject. Thus, a method is provided herein for increasing the trafficking of stem cells in a subject, comprising administering a therapeutically effective amount of a polysaccharide fraction of a blue green algae, thereby increasing the trafficking of stem cells in the subject.

Regardless of how provided or administered, the blue-green algae induces a transient increase in the population of circulating stem cells, such as CD34+ stem cells. Enhancement of stem cell trafficking may be measured by assaying the response of stem cells to a particular dose of blue-green algae. In one embodiment, providing blue-green algae to a subject will enhance mobilization of that subject's stem cells within a certain time period, such as less than about 5 hours, less than about 4 hours, less than about 2 hours, or less than about 1 hour following administration.

In one embodiment, administration of blue green algae results in the mobilization of stem cells into the circulation from about 2 to about 3 hours following administration. Mobilized stem cells will enter the circulatory system, thus increasing the number of circulating stem cells within the subject's body. The percentage increase in the number of circulating stem cells compared to a normal baseline may about 25%, about 50%, about 100% or greater than about 100% increase as compared to a control. In one embodiment, the control is a base line value from the same subject. In another embodiment, the control is the number of circulating stem cells in an untreated subject, or in a subject treated with a placebo or a pharmacological carrier.

In another embodiment, administration of an extract of blue green algae increases the rate of homing of stem cells measured by a transient decrease in the number of circulating stem cells within the subject's body. The percentage decrease in the number of circulating stem cells compared to a normal baseline may about 25%, about 50%, about 75%, or even about 100% as compared to a control. In one embodiment, the control is a base line value from the same subject. In another embodiment, the control is the number of circulating stem cells in an untreated subject, or in a subject treated with a placebo or a pharmacological carrier.

In some embodiments, the subject provided the blue-green algae is healthy. In other embodiments, the subject is suffering a disease or physiological condition, such as immunosuppression, chronic illness, traumatic injury, degenerative disease, or infection. In certain embodiments, the subject suffers a disease or condition of the skin, digestive system, nervous system, lymph system, cardiovascular system, or endocrine system. In specific embodiments, the subject suffers osteoporosis, Alzheimer's disease, cardiac infarction, Parkinson's disease, traumatic brain injury, multiple sclerosis, cirrhosis of the liver, or any of the diseases and conditions described in the Examples below.

EXAMPLES

The following examples are provided to illustrate particular features of various described embodiments. The scope of the present invention should not be limited to those features exemplified.

Example 1

Production of AFA

A blue green algae, such as *Aphanizomenon flos aquae* (AFA) is isolated from a source. In one embodiment, the source is a natural source of blue green algae, such as a lake (e.g. Klamath Lake). In another embodiment, the source is a man-made source of blue green algae such as an artificial lake or water source produced to grow and harvest blue green algae.

The blue green algae can be used directly, or can be stored as liquid, frozen liquid, freeze-dried, or dried using the method described below. In one embodiment, the blue green algae is harvested and dried using Refractance Window™ Technology. The term "Refractance Window™ Technology" refers to the fact that the dryer utilizes the very properties of water to drive water out of the product. In brief, when water is placed over a heating source, heat gets dispersed in the water through convection. As it absorbs heat, water transmits infrared energy to the outside in three ways: evaporation, conduction, and a little is transmitted through radiation. If the water's surface is covered by a transparent medium such as plastic, evaporation and its associated heat loss are blocked and only conduction occurs. The plastic membrane acts like a mirror reflecting infrared energy. But when a moist material is placed on the plastic surface, the water in the material creates a "window" that allows for the passage of infrared energy. For a brief moment, the water in the material allows for radiation, conduction and evaporation all to occur, providing for exceptionally effective heat transfer. However after a few minutes, as the material dries, the infrared "window" closes and conduction remains the only means of heat transfer. Since plastic is a poor heat conductor, little heat is lost and transferred to the product. Therefore, when dried with Refractance Window™ Technology, algae is exposed to heat for only a brief moment, delivering algae that is closest to its natural state.

Liquid algae is placed on the surface of the dryer's conveyor belt. The belt is a food grade mylar (transparent polyester film) set on the surface of hot water. Heat from the circulating water is conducted to the belt and then into the water present in the product to be dried, gently speeding the natural process of evaporation while protecting natural nutrients. As the product dries and water evaporates, heat ceases to be transmitted to the product. This prevents the degradation of polypeptides, nucleic acids, nutrients and pigments. Thus, the drying process maintains algae temperature far below the temperature of the circulating water beneath the conveyor belt.

Two factors play a role in the degradation of algae: degree of heat and exposure time to heat. Applying a high amount of heat for a short period of time results in less degradation of the components of the blue green algae. Thus, heat was applied to the algae at 72° C. for only 3 to 5 minutes. This process is known to one of skill in the art, and is fully described at the Rossha Enterprises Website, and is described in Abonyi et al., "Evaluation of Energy Efficiency and Quality Retention for the Refractance Window™ Drying System: Research Report, Washington State University, Pullman, Wash., Dec. 30, 1999).

Example 2

Stem Cells are Mobilized by AFA Consumption

Consumption of algae, *Aphanizomenon flos aquae* (AFA), or compounds thereof, enhances mobilization of CD34+ stem cells (see FIG. 1 for a diagram of stem cells entering the circulatory system).

Healthy human volunteers were identified, and the proportion of CD34+ cells was evaluated in the peripheral blood (circulating CD34+ cells) of each person prior to consumption of AFA and hourly for up to 4 hours after consumption. The volunteers were instructed to limit physical and mental activity for a time before and after consumption of AFA.

Each person was provided 5 g of dried AFA (see Example 1 for the method of drying). Red blood cells in whole blood samples obtained from each volunteer were lysed using FACS lysing solution (Beckton Dickenson, San Jose, Calif.). The remaining cells were washed and stained with monoclonal antibody HPCA-2 conjugated with fluorescein isothiocyanate. Samples were fixed in 1% formalin and analyzed by flow cytometry using a FacsCalibur flow cytometer (Becton Dickenson, San Jose, Calif.) and CellQuest software (Becton Dickenson, San Jose, Calif.).

Figure 2:
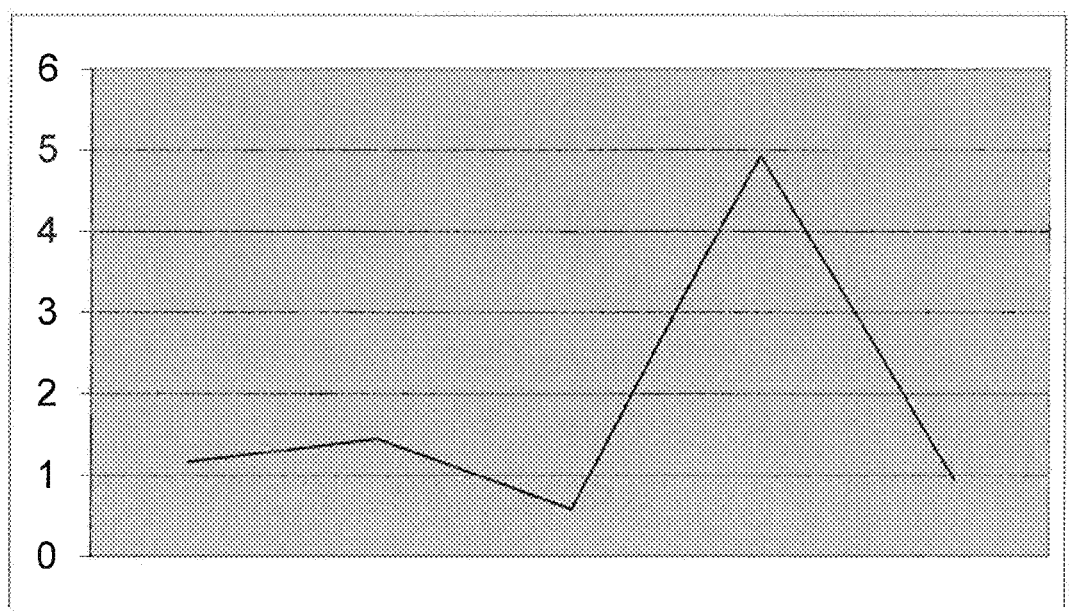
FIG. 2 is a graph illustrating a typical time course of stem cell activation in the human body after consumption of whole blue-green algae, *Aphanizomenon flos aquae* (AFA).

FIG. 2 illustrates that consumption of AFA triggered a strong transient increase in circulating stem cells. Specifically, the X-axis shows the time course of a typical experiment at 0, 1, 2, 3, and 4 hours after AFA ingestion, expressed as a percentage of the control level. At the time of ingestion, the proportion of circulating CD34+ cells is the same as the control. The peak increase in circulating CD34+ cells was observed at about 2-3 hours after consumption. At this time point, the number of circulating CD34+ cells was increased 4-fold (greater that 400%) over the control value. By 4 hours after AFA ingestion, the circulating CD34+ cells had returned to the baseline value.

Figure 3:
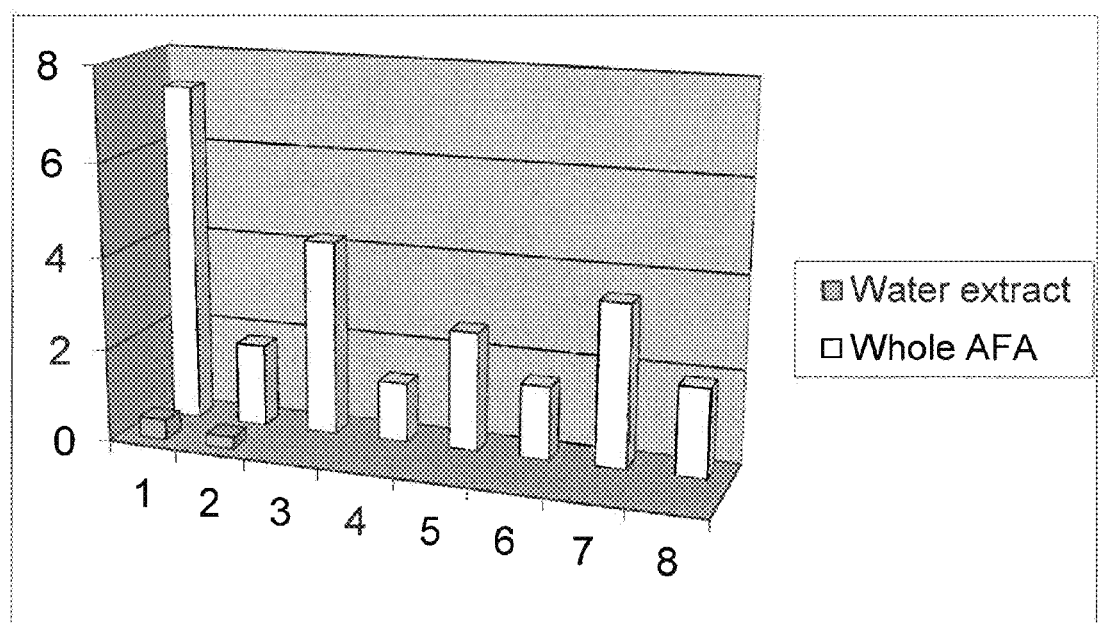
FIG. 3 is a graph illustrating a percentage increase of circulating CD34+ stem cells in the human body after ingestion of whole AFA compared to a water-soluble extract of AFA.
Figure 4A:
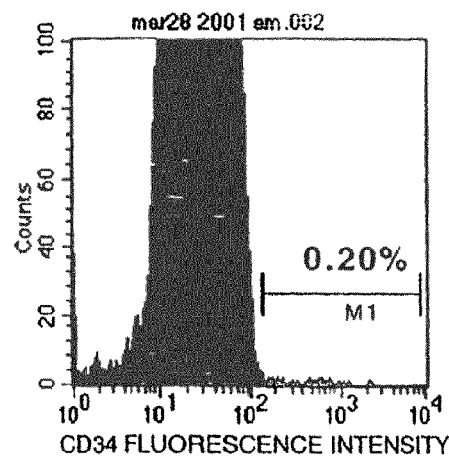
FIG. 4A-B are flow cytometry profiles of the expression of CD34 on small lymphocytes isolated from peripheral blood of a human volunteer. The X axis displays fluorescence intensity of the stem cell marker. The M1 marker indicates events showing positivity for the stem cell marker CD34.
Figure 4B:
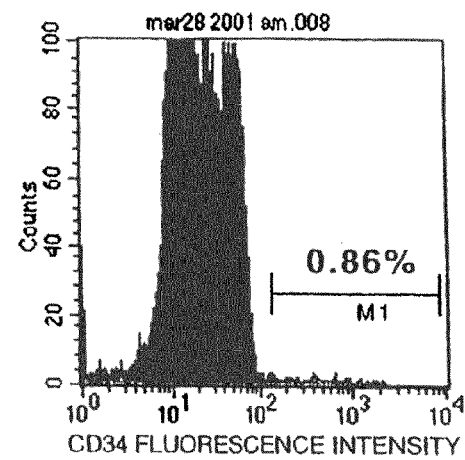

Therefore, AFA (or a biological component of AFA) can enhance the release of endogenous stem cells (e.g. CD34+ cells) from bone marrow and other anatomical sites into circulation. Consumption of AFA (or a biological component of AFA) mobilizes CD34+ stem cells (e.g., see FIGS. 3 and 4).

Example 3

Mobilized Stem Cells Retain Adhesion and Homing Phenotype

Figure 5:
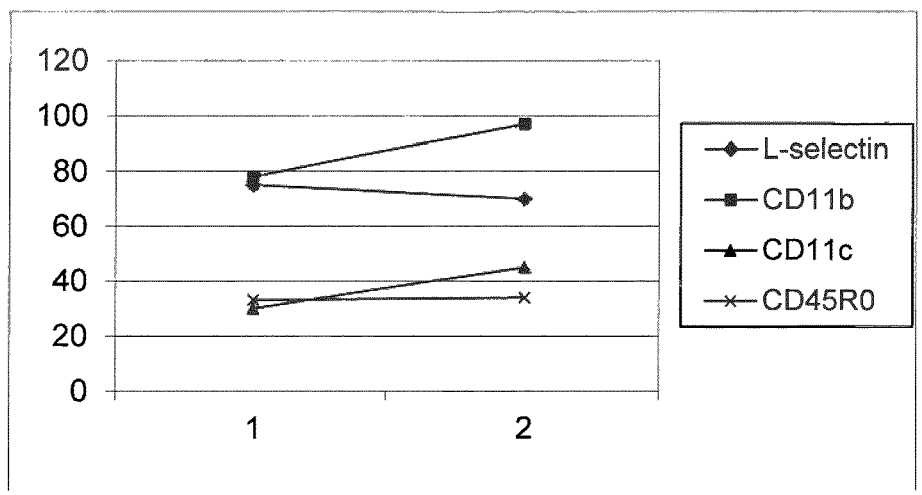
FIG. 5 is a graph illustrating the expression of adhesion and homing molecules on the surface of CD34+ circulating stem cells before and after consumption of AFA.

CD34+ cells mobilized into circulation by consumption of blue-green algae were evaluated for expression of adhesion and homing molecules on the cell surface. The following cell surface molecules were assayed in CD34+ cells before and after consumption: L-selectin (CD62L), CD11b, and CD11c. Additionally, the expression of CD45R0 was monitored to ensure the mobilized cells were of the same maturation stage as the CD34+ cells normally present in the circulation. The results illustrated in FIG. 5, wherein column 1 shows the number of cells expressing the designated marker prior to consumption of AFA, and column 2 shows the number of cells expressing the designated marker after consumption of AFA. The results demonstrate that the mobilized cells retain the phenotype with respect to these markers.

Example 4

Stem Cells from Bone Marrow Populate Multiple Distant Tissues

A murine model is chosen to evaluate the ability of stem cells mobilized by consumption of blue-green algae to populate distant tissues of the body.

Male mice are selected as bone marrow donor animals, while all recipient mice are females. Female recipients are sub-lethally irradiated prior to injection of male bone marrow cells into their tail veins. Two groups of mice are evaluated. The first group of 20 animals are sub-lethally irradiated, injected with bone marrow, and put on normal feed. The second group of 20 animals are also sub-lethally irradiated, receive male bone marrow, and are fed a diet of normal feed plus 15% w/v blue-green algae.

About $6 \times 10^6$ nucleated cells of adult bone marrow is harvested from male mice aged 8-10 weeks and injected into the tail veins of sub-lethally irradiated isogenic adult female recipients, also aged 8-10 weeks. Mice from each group are sacrificed at each of the following time points: time 0, 1 week, 2 weeks, 3 weeks, 4 weeks, and 8 weeks. At time points 2 and 8 weeks, 6 mice are sacrificed from each group. At all other time points, 2 mice are sacrificed from each group.

During the first two weeks after injection, 15 microliters of whole blood is taken from the ear, tail, or paw, and immediately diluted in 200 microliters of buffer (phosphate buffered saline, pH=7.2, 2% serum, o.02% azide) to dilute clotting factors and prevent coagulation. The blood samples are assayed to monitor the repopulation of platelets, red blood cells, and leukocytes within the blood. A portion of the blood sample is used for obtaining a cell count and for differential evaluation of red blood cells versus white blood cells. The sample is assayed using a flow cytometer, and the proportion of neutrophils, lymphocytes, and monocytes will be evaluated using forward and side scatter. The blood leukocytes will be examined for male origin using flow cytometry.

At time of sacrifice, various cell and tissue types will be examined for Hy antigen, which demonstrates that the cell or tissue originated in a male mouse. Brains are harvested and the entire brain is examined, including the olfactory bulb, hippocampus, cortical areas, and cerebellum. Bone marrow, heart muscle, hind leg muscle, liver, pancreas, sections of small intestine, and lung tissue are examined for presence of cells with Y chromosome, either by detection of surface Hy antigen by immunofluorescence, or by fluorescence in situ hybridization using probes for the Y chromosome. These data will document to what extent a diet containing blue-green algae promotes the homing, implantation, and differentiation process of the injected bone marrow stem cells.

Example 5

Stem Cells from Bone Marrow Populate Multiple Distant Tissues

A study similar to that of Example #3 is conducted using transgenic male mice carrying the gene for green fluorescent protein (GFP) and isogenic female mice as recipients. The animals are treated, fed, and sacrificed as in Example #3, and blood samples are also analyzed in a similar manner.

Blood leukocytes are examined for the expression of GFP using flow cytometry and, at time of sacrifice, various cell and tissue types will be examined for GFP antigen, which demonstrates the donor origin. Tissues and organs will be harvested as in Example #3 and the presence of cells carrying GFP is detected by green fluorescence microscopy.

Example 6

Increased Stem Cell Repopulation of Traumatized Tissue

A mouse model is used to evaluate homing and integration of bone marrow derived stem cells into traumatized tissue All marrow donors are adult male mice (8-10 weeks of age), and all recipient mice are adult females (8-10 weeks of age). Two groups of mice are evaluated. One group of sub-lethally irradiated recipients receive $6 \times 10^6$ nucleated donor cells via injection in the tail vein and allowed 2 weeks of recovery. The animals are then lightly traumatized by thin needle insertion into hind leg muscle, heart, and brain. All animals receive normal feed throughout the study. In the second group, female mice are treated identically as the first group, but are fed a diet that includes 15% w/v blue-green algae.

Two mice are sacrificed prior to trauma to evaluate baseline levels of male-derived cells. Subsequently, mice are sacrificed at the following time points: 1 week, 2 weeks, 3 weeks, and 4 weeks. Two mice are sacrificed for each time point, except for the 2 week time point, where 6 mice are sacrificed from each group. Hind leg muscle, heart, and brain tissue is isolated from the sacrificed animals. Sections are cut through the traumatized areas, and stained for male-derived cells using either cell surface marker analysis for the expression of the Hy antigen or by fluorescence in situ hybridization using probes for the Y chromosome. Alternatively, a GFP-expressing transgenic donor mouse will be used (similar to Example #4).

Data obtained demonstrate the effect of consuming blue-green algae on the speed of stem cell recruitment following trauma.

Example 7

Case Report for Tissue Repair

A 65-year old male with a lifelong history of a mildly compromised immune system (with recurrence of chicken pox five times during childhood) and inflammatory conditions during adulthood, including arthritis, demonstrated tissue repair in multiple body locations within about two weeks after beginning consumption of 1.5 g AFA per day.

Tissue repair occurred in muscle and dermal tissue on the forehead, lower back, and right knee. The back and knee were sites of prior surgery at ages 45 and 15, respectively. The subject suffered severe tissue damage to his forehead resulting from a car accident at age 25. This injury included an abundance of small glass splinters embedded in the skin and muscle of the forehead. After two weeks of regular AFA consumption, and approximately 40 years after this forehead injury occurred, about 30 small lesions formed on the subject's forehead, each containing a glass splinter. Once the glass splinters were expelled, the area healed with no further scarring.

Example 8

Case Report for Tissue Repair

A 52-year old female with a history of severe allergies and fibromyalgia was observed over a four-year period while consuming 1.5 g AFA per day for the first three years, and larger quantities during the fourth year. Observations of clinical symptoms of allergies, intense muscle pain associated with fibromyalgia, and microbial forms associated with red blood cells were conducted. A correlation exists between parasitized red blood cells and fibromyalgia/chronic fatigue syndrome. See, e.g., Nasraiia, M., et al., Eur. J. Clin. Microbiol. Infect. Dis., 18(12):859-65 (1999); Tarello, W., Comp. Immunol. Microbiol. Infect. Dis. 24(1):57-70 (2001); Vojdani A., et al., FEMS Immunol. Med. Microbiol., 22(4): 355-65 (1998); and Choppa, P. C., et al., Mol. Cell. Probes, 12(5):301-08 (1998).

Over the four-year period of observations, consumption of AFA increased the subject's tolerance to foods that previously initiated an anaphylactic reaction. AFA consumption also correlated to an increased proportion of non-parasiztized red blood cells versus parasitized red blood cells, thus improving delivery of oxygen to muscle tissue and reducing muscle pain. Thus, it appears AFA consumption stimulated hematopoietic cells to produce red blood cells.

Example 9

A High-Molecular Weight Polysaccharide Fraction of AFA Increased the Homing of Circulating Stem Cells Adult stem cells are continuously produced and enter circulation in humans. Increasing the rate or ability of stem cells to home to certain parts of the body has therapeutic applications, especially for many acute and chronic health problems.

Consumption of the blue-green algae Aphanizomenon fibs aquae (AFA) leads to a transient stem cell mobilization in humans, where within two hours after consumption, the amount of circulating stem cells is significantly increased. Consumption of a carbohydrate-rich fraction (designated "fraction A"), derived by mechanical separation of particulate matter from the water-soluble fraction, results in increased trafficking and homing of circulating stem cells in humans. This increased homing results in a reduced amount of stem cells in the peripheral blood within two hours after consumption.

Crude polysaccharide fraction was obtained using a simplified version of the method described by Pugh et al. (Planta Med 67:737-42 ((2001)). In brief, AFA was extracted for 4 hours with 70% ethanol at 65° C. The ethanol extract was centrifuged and then evaporated to dryness. The yield was approximately 30% of AFA original dry weight.

Standard immunostaining and flow cytometric techniques were used to detect circulating stem cells in the subjects. In brief, volunteers were kept resting in a sitting position, performing routine activities such as reading or writing, throughout the experiments, including an hour prior to baseline blood sampling. Blood samples were taken by venopuncture, and peripheral blood mononuclear cells obtained by Ficoll gradient centrifugation. Cells were washed in buffer containing serum and sodium azide to optimize fluorescent staining. Cells were stained using monoclonal antibodies for CD45 (to stain all white blood cells, in order to exclude contaminating red blood cells from analysis), CD34 (to stain circulating stem cells), CD3 and CD56 (to be able to analyze for CD3-CD56+ lymphocytes, which constitutes a major NK cell population), and appropriate isotype controls. Samples were fixed in 1% formalin and acquired on a FacsCalibur flow cytometer (Becton-Dickinson). Analysis was performed after gating for small lymphocytes and electronically excluding red cells, dead cells, monocytes, contaminating granulocytes, and any clumps of cells that may be present in the samples. Analysis was performed using the CellQuest software (Becton-Dickinson).

Whole AFA was administered at an amount of about 5 grams, and the water-soluble fraction was administered in an amount of 50 ml with a solid content of about 3% (thus, approximately 1.5 grams of solid were administered in the water-soluble extract). About three to five grams of the polysaccharide extract (fraction A) were administered.

Figure 6:
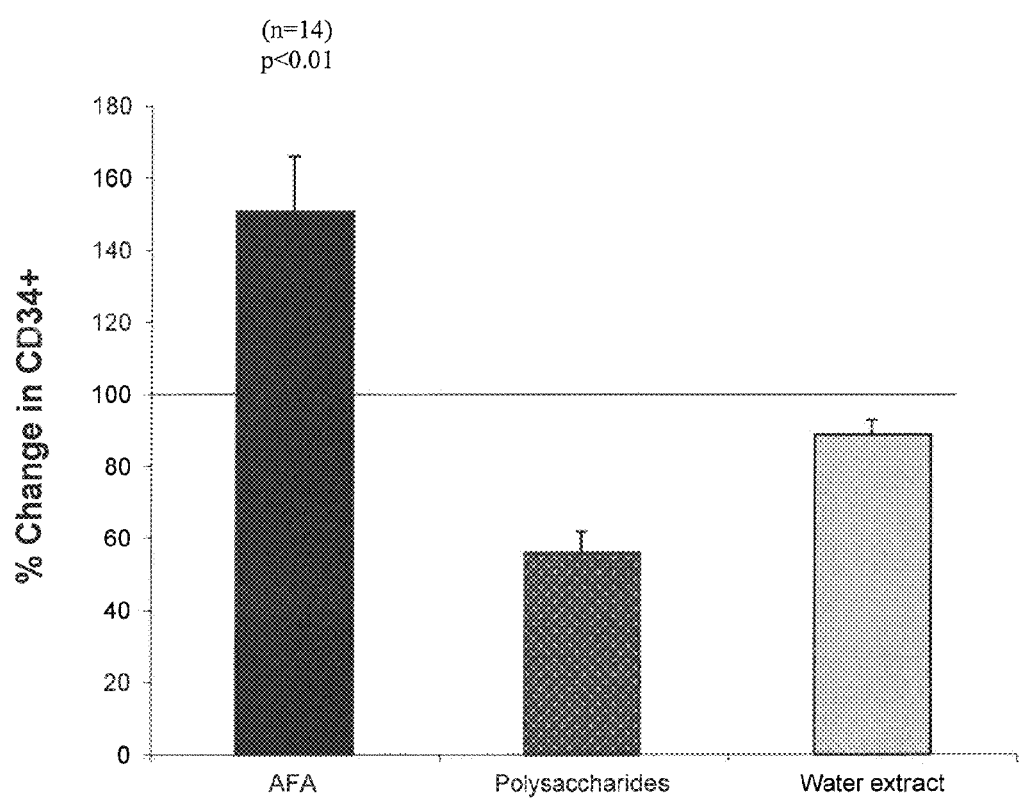
FIG. 6 is a graph illustrating the effects of consumption of whole AFA, a water-soluble phycocyanin-rich fraction of AFA, and a polysaccharide rich fraction (fraction A) of AFA on the number of circulating stem cells in human subjects.

Oral administration of fraction A, which contained the high-molecular weight polysaccharides, resulted in significant transient reduction in circulating stem cells in humans. Consumption of the water-soluble phycocyanin-rich fraction of AFA did not alter the number of circulating stem cells (see FIG. 6).

Figure 7:
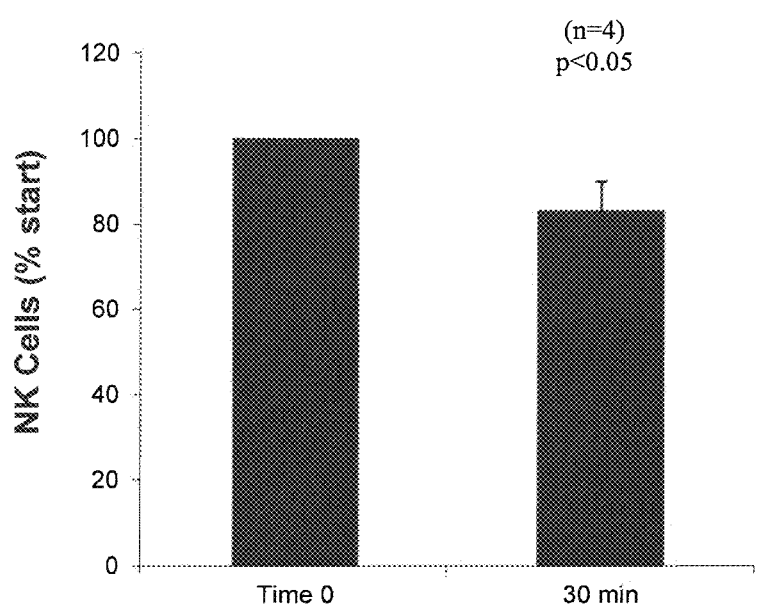
FIG. 7 is a graph illustrating that consumption the polysaccharide fraction (fraction A) of AFA resulted in a significant transient decrease in circulating Natural Killer (NK) cells in human subjects.

As shown in FIG. 7, consumption of this polysaccharide fraction also resulted in a significant transient decrease in circulating Natural Killer (NK) cells. This is in accordance with the previously described induction of homing of Natural Killer cells by oral consumption of *Aphanizomenon flos aquae* (see JANA 2:50-58, 2000).

Taken together, these data indicate that: consumption of whole AFA increases the number of stem cells in circulation; consumption of the water-soluble fraction does not affect the number of circulating stem cells; and consumption of the fraction rich in high-molecular weight polysaccharides from AFA (fraction A) results in increased homing of circulating stem cells and circulating NK cells.

Having illustrated and described the principals of the invention by several embodiments, it should be apparent that those embodiments can be modified in arrangement and detail without departing from the principals of the invention. Thus, the invention as claimed includes all such embodiments and variations thereof, and their equivalence, as come within the true spirit and scope of the claims stated below.

We claim:

1. A method for enhancing stem cell trafficking in a subject, comprising:
    selecting a subject with a disease or physiological condition, wherein the disease or physiological condition is cardiac infarction; and
    administering to the subject a therapeutically effective amount of *Aphanizomenon flos aquae*,
    thereby enhancing stem cell trafficking in the subject.

2. The method according to claim 1, wherein the subject is a mammal.

3. The method according to claim 1, wherein the subject is a human.

4. The method according to claim 1, wherein the *Aphanizomenon flos aquae* is administered as dried whole cells.

5. The method according to claim 1, wherein the *Aphanizomenon flos aquae* is administered as liquid fresh or frozen whole cells.

6. The method according to claim 1, wherein stem cell trafficking is increased about 100% to about 500% as compared to a control.

7. The method according to claim 1, wherein the stem cell is a CD34+ cell.

8. The method according to claim 1, further comprising measuring CD34+ stem cells in the subject.

9. A method for enhancing stem cell homing in a subject, comprising:
   selecting a subject with a disease or physiological condition, wherein the disease or physiological condition is cardiac infarction; and
   administering to the subject a therapeutically effective amount of *Aphanizomenon flos aquae*,
   thereby enhancing stem cell homing in the subject.

10. The method according to claim 9, wherein the subject is a mammal.

11. The method according to claim 9, wherein the subject is a human.

12. The method according to claim 9, wherein the *Aphanizomenon flos aquae* is administered as dried whole cells.

13. The method according to claim 9, wherein the *Aphanizomenon flos aquae* is administered as liquid fresh or frozen whole cells.

14. The method according to claim 9, wherein stem cell homing is increased about 100% to about 500% as compared to a control.

15. The method according to claim 9, wherein the stem cell is a CD34+ cell.

16. The method according to claim 9, further comprising measuring CD34+ stem cells in the subject.

17. A method of treating a subject with a disease amenable to treatment with stem cells, comprising:
   selecting a subject with a disease amenable to treatment with stem cells, wherein the disease is cardiac infarction; and
   administering to the subject a therapeutically effective amount of *Aphanizomenon flos aquae*,
   thereby treating the disease.

* * * * *